United States Patent [19]
Wiederrich

[11] Patent Number: 5,980,476
[45] Date of Patent: Nov. 9, 1999

[54] NON-COMPRESSIVE, DISTRACTING WRIST BRACE

[76] Inventor: Lester Arthur Wiederrich, 13440 St. Andrews Pl., Poway, Calif. 92064

[21] Appl. No.: 08/905,231

[22] Filed: Aug. 1, 1997

[51] Int. Cl.⁶ .................................................. A61F 5/00
[52] U.S. Cl. ................................................ 602/21; 602/64
[58] Field of Search .................................. 602/21, 60, 61, 602/62, 5, 64; 128/877, 878, 879; 473/59–63; 2/16, 159–162

[56] References Cited

U.S. PATENT DOCUMENTS

| | | | |
|---|---|---|---|
| Re. 24,627 | 5/1959 | Davini .................................... | 602/64 X |
| 680,477 | 8/1901 | Drosness .................................. | 602/64 |
| 1,790,381 | 1/1931 | Keller ..................................... | 602/64 |
| 3,117,786 | 1/1964 | Anderson ................................. | 602/21 |
| 5,538,501 | 7/1996 | Caswell .................................... | 602/64 |
| 5,672,151 | 9/1997 | Calderon-Garciduenas ............. | 602/21 |
| 5,695,453 | 12/1997 | Neal ....................................... | 602/64 X |
| 5,725,490 | 3/1998 | Conran .................................... | 602/64 X |
| 5,728,059 | 3/1998 | Wiesmann et al. ....................... | 602/64 |
| 5,733,249 | 3/1998 | Katzin et al. ............................. | 602/21 |

OTHER PUBLICATIONS

DuPuy Aluminum Hand Splint. 1937.

*Primary Examiner*—Jerome W. Donnelly
*Assistant Examiner*—Kim M. Lee

[57] ABSTRACT

A wrist brace designed to so that it makes body contact on a circumference at the butt of the hand and on a circumference around the arm at a location between the wrist and elbow. The design assures no circumferential compression to the arteries, nerves and other anatomical structures of the wrist.

5 Claims, 1 Drawing Sheet

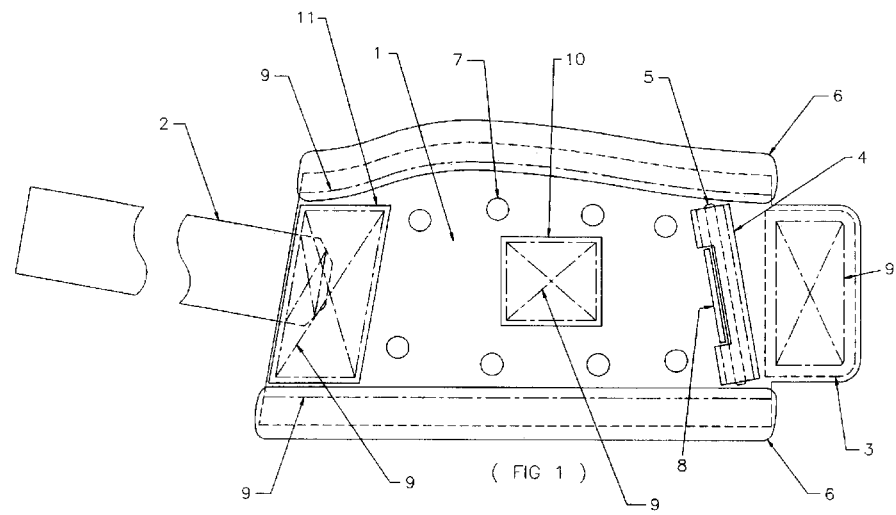
(FIG 1)
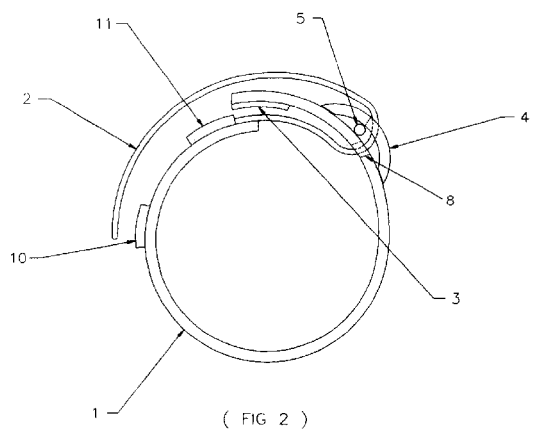
(FIG 2)
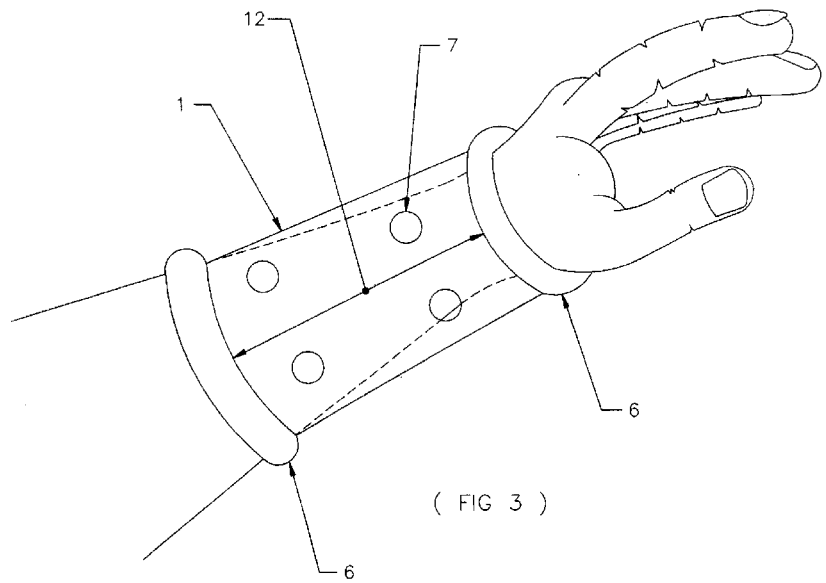
(FIG 3)

NON-COMPRESSIVE, DISTRACTING WRIST BRACE

BACKGROUND OF THE INVENTION

1. Field of the Invention

This invention relates to support braces and in particular to wrist support braces.

2. Background Art

Carpal tunnel syndrome is a serious condition caused by compression of the nerves of the wrist. Many modern day activities such as bicycle riding apply continuing compressive forces on the wrist, which can result in pain and possibly serious damage to the wrist. Prior art treatment for this condition includes the use of braces, which fit around the wrist to limit motion of the wrist. However, these prior art braces often aggravate the condition by further compressing the wrist tissue and in turn the nerves in the wrist.

SUMMARY OF THE INVENTION

The present invention provides a wrist brace designed so that it makes body contact on a circumference at the butt of the hand and on a circumference around the arm at a location between the wrist and the elbow. The design assures no circumferential compression to the arteries, nerves and other anatomical structures of the wrist. A generally rectangular sheet of stiff pliable material with padding material lining two opposite edges is wrapped around the wrist to form a tube with padding at both ends by the joining of the two unpadded edges. Only the padded ends make contact with the arm and the hand. A strap is provided for tightening the tube to apply compressing force at contact locations. No compressive force is applied at the wrist area. The brace provides partial immobilization of the wrist without compressing the wrist. Axial forces applied from the hand toward the elbow are dissipated toward the elbow through the brace instead of through the wrist to joint. When a person who is wearing the brace attempts to flex, extend or laterally bend the wrist, the brace will apply an axial distraction force thus reducing compression of the wrist joint. The brace is useful for avoiding carpal tunnel syndrome.

BRIEF DESCRIPTION OF THE DRAWINGS

FIG. 1 is a drawing of the preferred brace in an open flat view showing all its parts.

FIG. 2 is a drawing of the preferred brace in its rolled tube-shaped configuration showing the function of its locking system and securing strap.

FIG. 3 is a drawing showing the preferred brace in place on a human arm.

DETAILED DESCRIPTION OF PREFERRED EMBODIMENTS

The Brace

A preferred embodiment of the present invention is described by reference to the drawings. FIG. 1 is a drawing of a preferred embodiment of the present invention. It is a wrist brace. The body 1 of the brace is comprised of a pliable, durable plastic material about one sixteenth inch thick. It is generally rectangular in shape so that when wrapped around a wrist it virtually forms a rigid tube that is basically non-compressible in a longitudinal direction. Air holes 7 are provided to allow airflow around the wrist to provide cooling. A soft, skin friendly material 6 is stitched along two opposite edges of rectangularly shaped body 1 to form pads at both ends (a hand padded end and an arm padded end) of the tube. The two pads are the only contact of the brace with the skin, which is shown in FIG. 3. This contact is at the base of the hand (by the hand padded end) and on the lower arm about midway between the wrist and the elbow (by the arm padded end).

Locking Mechanism

This embodiment of the present invention provides a connecting, tightening mechanism for converting the rectangularly shaped body 1 into the tube-shaped brace and holding the brace tightly around the wrist without applying any compressive force to the wrist itself. As shown in FIGS. 1, 2 and 3, the soft loop portion of a first hook and loop fastener (preferably Velcro) is stitched to the lower side of tab 3 at one of the unpadded edges of body 1 as shown in FIGS. 1 and 2, and the hook portion 11 of the fastener is stitched to the upper side of body 1 as shown in FIGS. 1 and 2. Strap 2 comprised of the soft loop material of a second hook and loop fastener (also, preferably Velcro) is threaded through slot 8 as shown in FIG. 2 and looped around so that the soft side of strap 2 can contact a corresponding hook portion 10 of the second hook and loop fastener. The now tubular-shaped brace is then slipped over the hand and lower arm of a user and tightened as shown in FIG. 3 in the manner indicated in FIG. 2. It is locked in place over the wrist at the position shown in FIG. 3 by pressing loop portion of the first fastener on tab 3 against hook portion 11 and pressing the loop portion (strap 2) of the second fastener against hook portion 10 as indicated in FIG. 2.

Advantages

The brace is designed so that it only makes two areas, i.e., at a circumference around the butt of the hand and at a circumference around the arm about midway between the wrist and the elbow. This design assures no circumferential compression to anatomical structures of the wrist such as arteries and nerves with the carpal tunnel. The brace provides non compressive immobilization of the wrist. Attempts at flexing, extending or bending the wrist will apply an axial distracting force at the wrist tending to reduce any compressive force on the wrist. Thus, axial forces applied to the hand in the direction of the elbow, such as the force on the wrist experienced when riding a bicycle will in part be dissipated through the brace to the upper arm to reduce compressive forces on the wrist.

The above description of a preferred embodiment is presented for illustration. It is not intended to be exhaustive. Many modifications and variations are possible in light of the above teaching. It is intended that the scope of the present invention be limited not by the abpve descriptions, but rather the claims appened hereto.

What is claimed is:

1. A wrist brace for bracing human user's wrist with pressure applied at the but of the user's hand and arm, said brace comprising:
   a) a generally rectangularly shaped body, defining two soft edges and tow connecting edges, and comprised of a sheet of stiff material but pliable enough so that when not in use it can be un-wrapped from the wrist and when used can be wrapped around the wrist into a tubular shape connecting edges;
   b) padding means lining said two soft edges to pad soft edges;
   c) a connecting, tightening means for:

1. connecting said two connecting edges to form a tubular-shaped brace, defining a hand padded end and an arm padded end, and 2. tightening said brace around said wrist with compressive force being applied circumferentially (I) between said hand padded end and said user's hand and (ii) between said arm padded end and said user's arm, about midway between said user's wrist and elbow, with no compressive forces being applied to said user's wrist, wherein, during use said brace makes firm contact at only the butt of the hand which in turn transfers that pressure longitudinally in the brace to the point where contact is made of the forearm causing traction forces to occur on the internal structures of the wrist.

2. A wrist brace as in claim 1 wherein said tightening means comprises at least one hook and loop fastener.

3. A wrist brace as in claim 2 wherein said tightening means contains two hook and loop fasteners.

4. A wrist brace as in claim 3 wherein one of said two hook and loop fasteners comprise a strap comprised of loop material.

5. A wrist brace as in claim 1 wherein said body comprises a plurality of ventilation holes.

* * * * *